United States Patent
Salmelainen et al.

(10) Patent No.: US 9,429,469 B2
(45) Date of Patent: Aug. 30, 2016

(54) APPARATUS AND METHOD FOR MEASURING OPTICAL COMPONENT

(71) Applicant: Labrox Oy, Turku (FI)

(72) Inventors: Pauli Salmelainen, Masku (FI); Antero Yli-Koski, Piikkiö (FI)

(73) Assignee: Labrox Oy, Turku (FI)

( * ) Notice: Subject to any disclaimer, the term of this patent is extended or adjusted under 35 U.S.C. 154(b) by 110 days.

(21) Appl. No.: 14/407,050

(22) PCT Filed: Jun. 7, 2013

(86) PCT No.: PCT/FI2013/050619
§ 371 (c)(1),
(2) Date: Dec. 10, 2014

(87) PCT Pub. No.: WO2013/186435
PCT Pub. Date: Dec. 19, 2013

(65) Prior Publication Data

US 2015/0177060 A1  Jun. 25, 2015

(30) Foreign Application Priority Data

Jun. 11, 2012  (FI) ..................................... 20125637

(51) Int. Cl.
*G01J 1/04* (2006.01)
*G01J 1/42* (2006.01)
*G01N 21/64* (2006.01)

(52) U.S. Cl.
CPC ............ *G01J 1/4228* (2013.01); *G01J 1/0444* (2013.01); *G01N 21/645* (2013.01); *G01N 21/6452* (2013.01); *G01N 2021/6471* (2013.01); *G01N 2201/02* (2013.01)

(58) Field of Classification Search
CPC .... G01J 1/42; G01J 1/043; G01J 2003/2866; G01J 21/64
USPC ....... 250/221, 559.1, 216; 356/364–369, 326
See application file for complete search history.

(56) References Cited

U.S. PATENT DOCUMENTS 4,396,288 A  8/1983  Helphrey
5,123,735 A  6/1992  Hegarty (Continued)

FOREIGN PATENT DOCUMENTS

DE  207984 A1  3/1984
EP  0803724 A2  10/1997

(Continued)

OTHER PUBLICATIONS

Zhang, Z. M. et al: Standard Reference Materials: Transmission filters with measured optical density at 1064 nm wavelength-SRMs 2046, 2047, 2048, 2049, 2050, and 2051. NIST Special publication—260-128, 1998, pp. 5-7, 17; fig. 1.

(Continued)

*Primary Examiner* — Que T Le
(74) *Attorney, Agent, or Firm* — Ziegler IP Law Group, LLC (57) ABSTRACT

An apparatus for measuring an optical component (160, 170, 190) of the apparatus, the apparatus comprising a radiation source (130) configured to form a measuring beam in a measuring channel (140), wherein the measured optical component configured to be in a first position outside the measuring channel and in a second position in the measuring channel; a first detector (110) configured to receive beams in the measuring channel; a second detector (150) configured to receive beams in the measuring channel; at least one processor; and at least one memory including computer program code. The at least one memory and the computer program code are configured to, with the at least one processor, cause the apparatus at least to select at least one of the first detector and the second detector to receive beams in the measuring channel, the measuring channel (140) being integrated to a photometer or a fluorescence channel of the apparatus; receive a first beam, using the selected detector, in the measuring channel, wherein the measured optical component is in the first position; receive a second beam, using the selected detector, in the measuring channel, wherein the measured optical component is in the second position; and determine the characteristics of the optical component based on the first beam and the second beam.

14 Claims, 3 Drawing Sheets

(56) References Cited

U.S. PATENT DOCUMENTS

| | | |
|---|---|---|
| 7,145,652 B2 | 12/2006 | Moehler et al. |
| 8,766,165 B1 * | 7/2014 | Zhovnirovsky .... G01M 11/0264 250/208.1 |

FOREIGN PATENT DOCUMENTS

| | | |
|---|---|---|
| EP | 1355182 A1 | 10/2003 |
| EP | 1650589 A1 | 4/2006 |

OTHER PUBLICATIONS

Durrheim, C. R., "The Fluorescent Tube-Lamp Integrating Chamber", University of KwaZulu-Natal, thesis submitted in partial fulfillment for the degree of Master of Science in the School of Physics, 2008, pp. 112-117.

Purdy, P.P., "Cavity QED with Ultracold Atoms on an Atom Chip", University of California, dissertation submitted in partial satisfaction for the degree of Doctor of Philosophy in Physics in the Graduate Division of the University of California Berkley, Fall 2009, section A.2.1.

Ghinassi, F. et al. Transmission curves and effective refraction indices of MKO near infrared consortium filters at cryogenic temperatures. 2002, vol. 386, pp. 1157-1159 section 2; figs. 1-2.

K Mackrodt et al: "Automated optical filter measurement inspection and mapping system", Jun. 27, 2004, XP055123813, Retrieved from the Internet: URL:http://www.opticsinfobase.org/DirectPDFAccess/A3CAD8F2-EF79-0F0D-7D49446B9EBEFDF8_112862/OIC-2004-ThB8.pdf?da=1&id=112862&uri=OIC-2004-ThB8&seq=0&mobile=no [retrieved on Jun. 17, 2014].

Transmittal of International Search Report and Written Opinion; PCT/FI2013/050619; mailed Sep. 9, 2013 (11 pages).

Written Opinion of the International Preliminary Examining Authority; PCT/FI2013/050619; mailed Jun. 25, 2014 (8 pages).

Transmittal of the International Preliminary Report on Patentability; PCT?FI2013/050619; mailed Sep. 25, 2014 (20 pages).

* cited by examiner

APPARATUS AND METHOD FOR MEASURING OPTICAL COMPONENT

TECHNICAL FIELD

The present invention generally relates to an apparatus measuring an optical component. The invention relates particularly, though not exclusively, to measuring optical characteristics of a component of a microtiter plate reader.

BACKGROUND ART

Presently, microtiter plate readers with separate filter slides for excitation filters and emission filters are known. Apparatuses for irradiating samples which can be characterized by light penetrating the samples (transmission), the light reflected by the samples (reflection), light initiated on or in the sample (fluorescence) or light emitted by the samples themselves (luminescence) have been known as microscopes, spectrophotometers, fluorometers and the like. The light that penetrates the sample during the irradiation or is reflected by the same or the fluorescence initiated on or in the sample will be designated below as "light originating from the sample" and will be measured for example by one or several photodetectors. The use of different optical filters for influencing light rays with which the samples are radiated or light that is transmitted through the same (so-called excitation filters) is known. Similarly, emission filters are known which influence the light emitted by the samples. Furthermore, dichroic mirrors are known which reflect certain wavelengths and passes other wavelengths.

Since optical components, such as filters or mirrors, may be exchanged by a user of the apparatus, the components need to be identified. Identification labels may be attached to the components to provide information of the components. However, automatic identification of components is desired. Such automatic identification may be utilized using bar codes, for example. Using bar codes the apparatus may identify the optical components. However, even such solution does not provide any further information on the optical component characteristics than what is inserted to a database of the system. Bar codes are also troublesome for user's own components that do not support similar bar codes as the apparatus manufacturer. Thus it is desired to have an apparatus and a method for automatically identifying an optical component of the apparatus and also enables a reliable identification of user's own optical components.

SUMMARY

According to a first example aspect of the invention there is provided an apparatus for measuring an optical component of the apparatus, the apparatus comprising:
  a radiation source configured to form a measuring beam in a measuring channel, wherein the measured optical component configured to be in a first position outside the measuring channel and in a second position in the measuring channel;
  a first detector configured to receive beams in the measuring channel;
  a second detector configured to receive beams in the measuring channel;
  at least one processor; and
  at least one memory including computer program code, the at least one memory and the computer program code being configured to, with the at least one processor, cause the apparatus at least to:
    select at least one of the first detector and the second detector to receive beams in the measuring channel, the measuring channel being integrated to a photometer or a fluorescence channel of the apparatus;
    receive a first beam, using the selected detector, in the measuring channel, wherein the measured optical component is in the first position;
    receive a second beam, using the selected detector, in the measuring channel, wherein the measured optical component is in the second position; and
    determine the characteristics of the optical component based on the first beam and the second beam.

In an embodiment, the at least one memory and the computer program code being further configured to, with the at least one processor, cause the apparatus to:
  store the characteristics of the optical component to the memory; and
  provide the optical component to be used by a user of the apparatus.

In an embodiment, the optical component is a filter, band-passing the second beam to the first detector; and
  the at least one memory and the computer program code being further configured to, with the at least one processor, cause the apparatus to:
  determine the characteristics of the filter based on the first beam and the second beam, wherein the characteristics comprise band-pass wavelength information.

In an embodiment, the optical component is a dichroic mirror, reflecting the second beam to the first detector; and
  the at least one memory and the computer program code being further configured to, with the at least one processor, cause the apparatus to:
  determine the characteristics of the dichroic mirror based on the first beam and the second beam, wherein the characteristics comprise reflection wavelength information.

In an embodiment, the optical component is a dichroic mirror, transmitting the second beam to the first detector; and
  the at least one memory and the computer program code being further configured to, with the at least one processor, cause the apparatus to:
  determine the characteristics of the dichroic mirror based on the first beam and the second beam, wherein the characteristics comprise transmittance wavelength information.

In an embodiment, the apparatus further comprises a second detector, configured to receive beams in the measuring channel; wherein
  the at least one memory and the computer program code being further configured to, with the at least one processor, cause the apparatus to:
  select at least one of the first detector and the second detector to receive beams in the measuring channel.

In an embodiment, the at least one memory and the computer program code being further configured to, with the at least one processor, cause the apparatus to:
  receive a third beam, using the second detector, in the measuring channel, wherein the measured optical component is in the second position; and
  determine the characteristics of the optical component using the first beam and the third beam.

In an embodiment, the first detector comprising at least one of the following:
  a photometer detector;
  a fluorescence detector;
  a spectrograph;

a photodiode; and a photo multiplier tube.

In an embodiment, the second detector comprising at least one of the following:

a photometer detector;

a fluorescence detector;

a spectrograph;

a photodiode; and a photo multiplier tube.

In an embodiment, the measuring channel comprising at least one of the following:

a fluorescence channel of a microtiter plate reader;

a photometer channel of a microtiter plate reader;

an emission channel of a microtiter plate reader; and an excitation channel of a microtiter plate reader.

In an embodiment, the first position comprising a storage position for the optical component in the apparatus.

According to a second example aspect there is provided a method for measuring characteristics of an optical component of an apparatus, the method comprising:

generating a measuring beam in a measuring channel using a radiation source;

selecting at least one of a first detector and a second detector to receive beams in the measuring channel, the measuring channel being integrated to a photometer or a fluorescence channel of the apparatus;

receiving a first beam, using a first detector, in the measuring channel, wherein the measured optical component is in a first position outside the measuring channel;

receiving a second beam, using the first detector, in the measuring channel, wherein the measured optical component is in a second position in the measuring channel; and determining the characteristics of the optical component based on the first beam and the second beam.

In an embodiment, a second detector may be used for receiving the second beam.

According to a third example aspect there is provided a computer program embodied on a computer readable medium comprising computer executable program code which, when executed by at least one processor of an apparatus, causes the apparatus to perform the method of the second example aspect.

Different non-binding example aspects and embodiments of the present invention have been illustrated in the foregoing. The above embodiments are used merely to explain selected aspects or steps that may be utilized in implementations of the present invention. Some embodiments may be presented only with reference to certain example aspects of the invention. It should be appreciated that corresponding embodiments may apply to other example aspects as well.

BRIEF DESCRIPTION OF THE DRAWINGS

The invention will be described, by way of example only, with reference to the accompanying drawings, in which.

DETAILED DESCRIPTION

In the following description, like numbers denote like elements.

In an embodiment, an apparatus may comprise a detector, such as a photometer detector for measuring passing through of a light with desired wavelengths. The photometer detector may be a spectrograph, for example. The detector may also comprise a fluorescence detector or a photodiode, which provides spectral information when used together with a monochromator, for example. The apparatus may identify the optical components based on the band pass information of the measured component and utilize the component automatically without user interaction. The band pass information of the measured component may be used to calculate mirror reflected portion of the light or the filter absorbed portion of the light, for example. Measuring the optical component of the apparatus enhances the information for the component in addition to the identification of the component. Even manufacturing based tolerances or errors for the same component may be measured and informs the real performance of the component.

Figure 1:
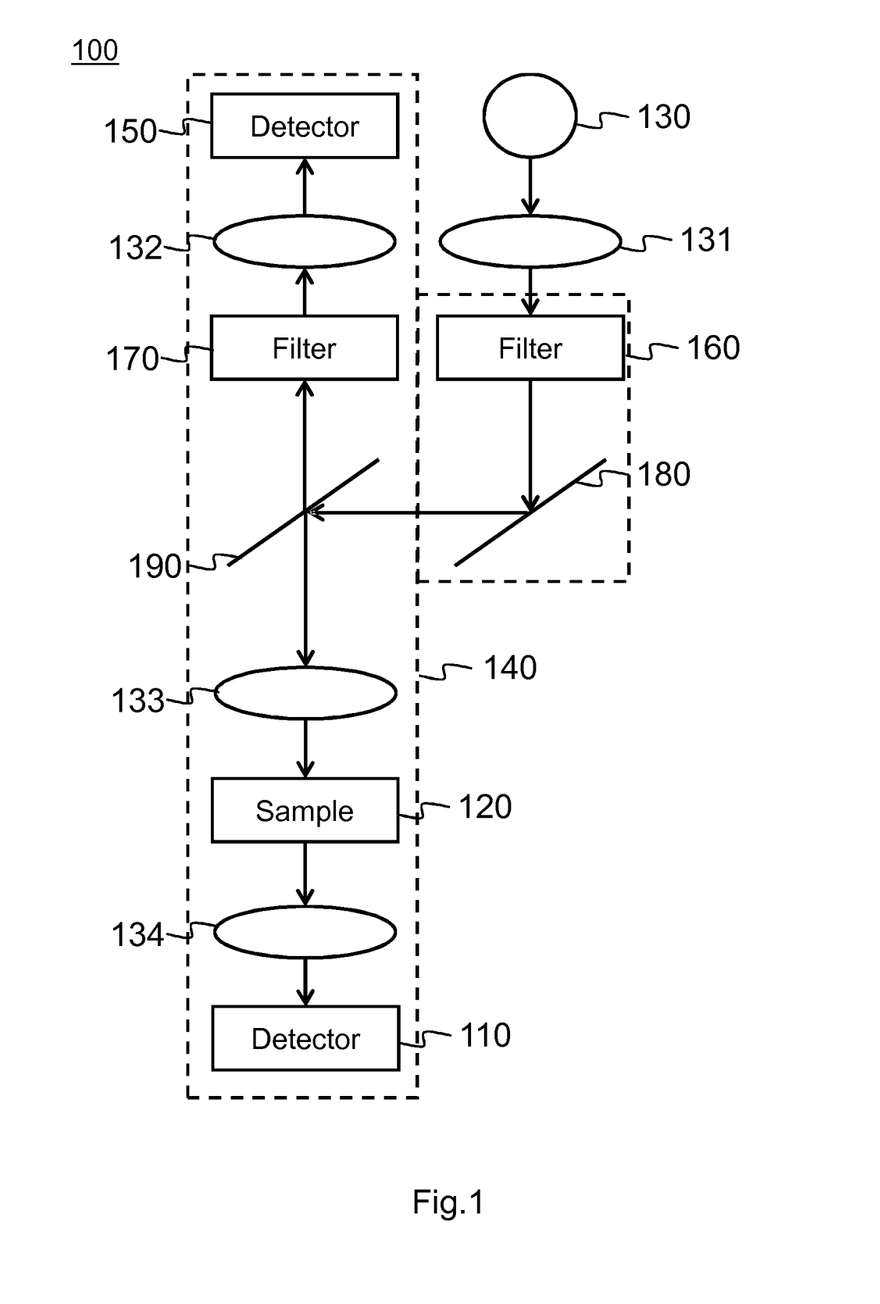
FIG. 1 shows a schematic picture of a measuring arrangement of an optical component in an apparatus according to an example embodiment of the invention.

FIG. 1 shows a schematic picture of a measuring arrangement 100 of an optical component 160, 170, 190 in an apparatus according to an example embodiment of the invention. In an embodiment, the measured component 160, 170, 190 may comprise for example a filter or a dichroic mirror. Transmittance of the component 160, 170 and reflectance of the component 190 may be measured within wide enough band wavelength to provide reliable data. The transmittance may be determined using a detector 110 and the absorbance can be determined using this information. The first detector 110 in FIG. 1 may comprise a spectrograph for example. A second detector 150 may comprise a photomultiplier tube or a photo diode, for example, for converting light into an electrical signal for processing. The second detector 150 may be used to measure emission of light from the measured sample 120.

In an embodiment, a radiation source 130, such as a light source, is configured to form a measuring beam in a measuring channel 140. The radiation source 130 may be capable of producing wide spectrum of light. The radiation source 130 may be a polychromatic light source, such as a halogen lamp or a xenon flash lamp, for example. Together with an excitation filter 160 of certain optical characteristics, desired excitation light may be generated. Optics 131-134 may comprise at least one lens that may be positioned between the light source 130 and the detectors 110, 150 to focus and re-size the light beam to a desired size and separate channels.

In an embodiment, a beam produced by the radiation source 130 may be filtered by an excitation filter 160. The filter may be an interference filter, a colored glass filter or a combination of both, for example. The excitation filter 160 may be used for band-passing a certain center wavelength band from the excitation radiation. The measuring beam may be directed to the measuring channel in various ways. One alternative is illustrated in FIG. 1 by using mirrors 180, 190. The mirror 190 may be changeable and at least one of the mirrors 190 may be a dichroic mirror or a beam splitter which reflects a portion of the incident light with full spectrum and transmits the rest. The dichroic mirror 190 reflects certain wavelengths and passes other wavelengths through. In FIG. 1 the mirror 180 is used merely to turn the light direction and it is not necessarily needed.

In an embodiment, an emission filter 170 may be used for detecting emission light from the sample 120 using the detector 150.

In an embodiment, a measured component 160 is first removed from a measuring channel 140. A light beam is directed from a light source 130 through the channel 140 to a detector 110 via a lens 131, mirrors 180, 190 and lenses 133-134, for example. A sample 120, comprising a microtiter plate for example, may be removed from the channel 140. The measured component 160 may be an excitation filter normally located in position 160 when measuring a sample 120. The measured component 160 may also be an emission filter normally located in position 170 when measuring the sample 120. The measured component may also be a mirror 190. In case the mirror 190 comprises a dichroic mirror, the reflected portion of light may be measured and the passed through portion can be calculated from that information. The instrument geometry can also differ from the geometry in FIG. 1 and the transmittance of the dichroic mirror can be measured and the reflectance can be calculated from the transmittance information. The reflected portion in FIG. 1 may be measured using a first detector 110. In FIG. 1, the second detector 150 is positioned above the mirror 190 only for illustrative purposes but may be located in any direction of the mirror 190 where either sample excitation or emission light passing through the mirror 190 may be directed.

In an embodiment, the reflected beam from the normal mirror 190 is directed in a first measurement to a first detector 110, such as a spectrograph or a combination including a monochromator and a suitable detector like photomultiplier tube or photodiode. An optical lens 133, 134 may be used between the mirror 190 and the detector 110. The first measurement thus provides a reference value of the measurement beam in the measuring channel 140. In a second measurement, the measured component 160 is positioned to the measuring channel 140 between the lens 131 and the mirror 180, for example. The beam may be directed from the mirror 190 to the detector 110. At least one optical lens 133, 134 may be used between the mirror 190 and the detector 110.

In an embodiment, the measured component may be moved between a storage position outside the channel 140 and the measuring position in the channel 140 using a dynamic component transfer mechanism. The mechanism may move excitation and emission filters to position 160 of FIG. 1 and reflecting and dichroic mirrors to position 190 of FIG. 1, for example.

In an embodiment, the mirror 190 may comprise a reflecting mirror, a dichroic mirror or a beam splitter. The beam splitter may reflect a certain portion of the incident light. In case a dichroic mirror 190 is used when measuring component 160, characteristics of the dichroic mirror 190 needs to be known to be able to calculate optical characteristics of the measured component 160.

In an embodiment, when a measured component is a dichroic mirror 190, a first measurement may be done without the excitation filter 160 and a reflecting mirror is placed to the position 190 for reference value measurement. A second measurement may be done without the excitation filter 160 but the measured dichroic mirror is placed to the position 190. Based on the first and second measurement optical characteristics (reflection/pass through wavelengths) of the dichroic mirror 190 may be determined.

In an embodiment, when a measured component is a filter (emission or excitation), the measured filter is removed from a filter position 160 and a first measurement may be done with a reflecting mirror being placed to the position 190 for reference value measurement. A second measurement may be done by placing the measured filter to position 160. Based on the first and second measurement optical characteristics (band passing wavelengths) of the filter 160 may be determined.

The first and second measurements provide first and second spectrum information, respectively. By comparing these two spectrum information, band passing characteristics of the component 160, 190 may be determined. The component 160, 190 may absorb or reflect part of the measuring beam, as well as combine absorption and reflection. An absorption curve can be calculated for the component 160, 190 and furthermore a passing curve that defines how well the component 160, 190 passes light with a certain wavelength. When measuring the optical characteristics of the component 160, 190 either the passing curve, the absorption curve, parts of the curves or some dedicated wavelengths may be used.

In an embodiment, an optical filter used as the measured component 160, typically passes light beams within certain wavelengths and absorbs light beams outside those wavelengths. The optical filter 160 is typically matched with as wide wavelength scale as the used detector 110, for example the photometer detector.

In an embodiment, a dichroic mirror used as the measured component 190, typically reflects light beams within certain wavelengths and passes through light beams outside those wavelengths. For example, short wavelengths may be reflected and long wavelengths passed, or vice versa. Based on the first (with a reflecting mirror 190) and second measurement (with dichroic mirror 190), the band passing (or reflecting) wavelengths for the dichroic mirror 190 may be determined in similar fashion as described above.

In an embodiment, the reflection wavelengths for the mirror 190 may be determined to comprise wavelengths outside the determined band passing wavelengths. Such determination assumes that the mirror 190 does not absorb any wavelengths.

In an embodiment the measurement of the dichroic mirror 190 may be done by measuring the transmitted wavelengths instead of the reflected wavelengths and determine the reflected wavelengths based on the measured transmitted wavelengths. In the instrument there can be several measurement channels and the detector 110 may (unlike in FIG. 1) be located so that it can measure the transmitted wavelengths of the mirror 190.

In an embodiment, the measurement of the dichroic mirror 190 may be done by measuring the reflected wavelengths using a first detector 110 in the measuring channel 140. The first detector 110 may detect the reflected beams from the measured mirror 190 and the band passing wavelengths of the mirror 190 may be determined based on the measured reflected wavelengths. Such determination may assume that non-reflected wavelengths are band passed, for example, In an embodiment, an emission filter 170 may be used for band-passing a certain center wavelength band from the emission radiation of a measured sample 120. Furthermore, an optical lens 132 may be used between the second detector 150 and the filter 170.

In an embodiment, a measured component may be placed in place of a filter 170. A light beam may travel from a light source 130 to a second detector 150 via reflection by at least one mirror 180, 190. A first measurement may be done without the filter 170 and a second measurement with the filter 170. Furthermore, a set of lenses 131, 132 and a filter 160 may be used, as well as a further mirror, for example.

In an embodiment an emission filter 170 can be automatically moved to the position 160 and be measured with similar way than described above.

In an embodiment, an emission filter 170 may also be located between the measured sample 120 and the photometer detector 110. Emission spectrum may be determined for the sample 120 using the detector 110, such as a spectrograph, for example.

Measuring of the optical component 160, 170, 190 provides enhanced accuracy and reliability for the characteristics of the optical component. Error tolerances informed by the manufacturer of the component 160, 170, 190 may be reduced and wider range of component characteristics may be determined compared to the information provided by the manufacturer. This is especially useful when the component 160, 170, 190 is used for accurate measurements of other usages than the component 160, 170, 190 is originally targeted for.

An apparatus, such as a microtiter plate reader, comprising the measuring arrangement 100 provides an automatic and accurate method to identify the optical characteristics of optical components 160, 170, 190 used in the apparatus. All the selectably used components 160, 170, 190, such as filters and dichroic mirrors, may be measured using the arrangement 100. The measured characteristics may be stored to the memory of the apparatus and stored to a component storage, such as filter wheel, for example. The location of the component 160, 170, 190, in the storage, may be linked to the measured characteristics and thus the apparatus knows all the time the accurate characteristics of each component 160, 170, 190 stored in the storage.

In an embodiment, the measuring channel 140 may be integrated to a photometer or a fluorescence channel of the apparatus. Alternatively, the measuring channel 140 may be provided as a separate measuring channel in the apparatus.

An apparatus of a microtiter plate reader uses a set of optical components, such as filters or dichroic mirrors, used for excitation, reflection, band passing and emission. In an embodiment of the invention, the apparatus comprises at least one storage for the filters and a mechanism to move the filters between the storage and the measuring channel 140. Furthermore, a computer system for controlling the optical component 160, 170, 190 operation and exchange is provided. A user of the apparatus may be provided a list of optical components in the storage with their optical characteristics, and based on the user's selections the computer system may control the mechanism to operate the desired components 160, 170, 190 of the apparatus.

In an embodiment, the optical component 160, 170, 190 is an optical filter operating on a band around a certain center wavelength of radiation, for example light. Furthermore, high-pass and low-pass filters may be used. The optical filter may be an interference filter, a colored glass filter or a combination of both, for example. An excitation filter may be used for bandpassing a certain center wavelength band from the excitation radiation provided by a radiation source, such as a light source. An emission filter may be used for bandpassing a certain center wavelength band from the emission radiation from a sample in response to the excitation radiation. The optical component may also be a dichroic mirror or a beam splitter. The dichroic mirror reflects certain wavelengths and transmits other wavelengths. The beam splitter reflects a certain portion of all wavelengths and transmits the remaining portion.

Figure 2:
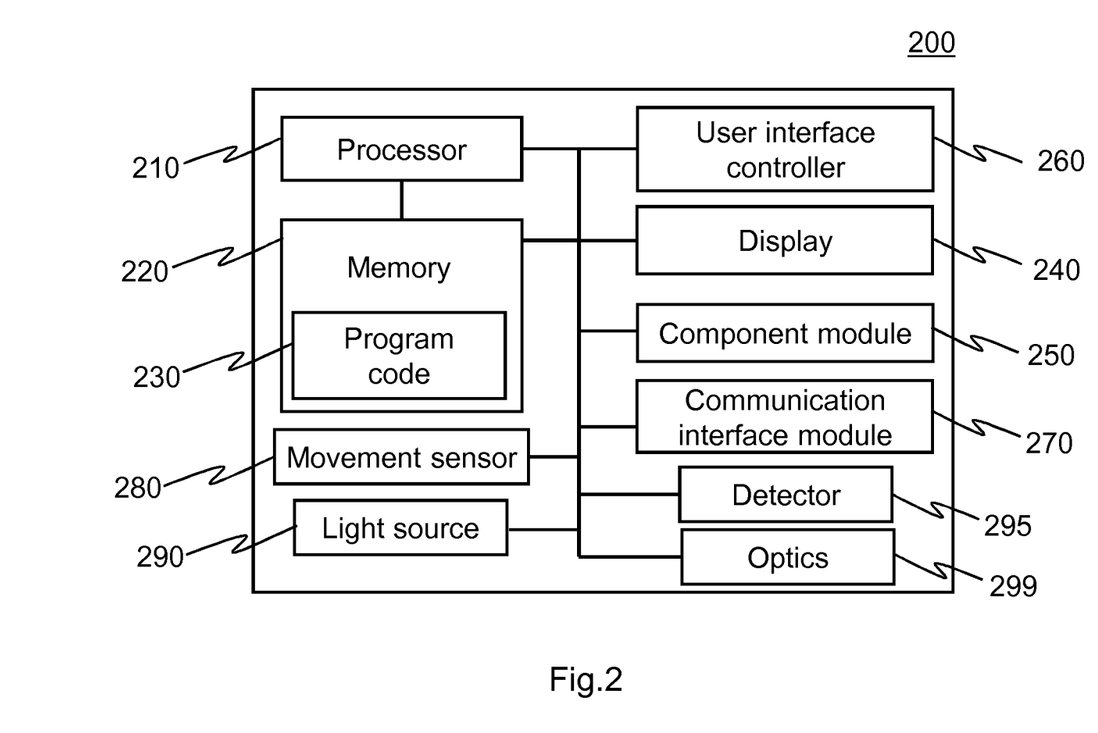
FIG. 2 presents an example block diagram of an apparatus in which various embodiments of the invention may be applied.

FIG. 2 presents an example block diagram of an apparatus 200 in which various embodiments of the invention may be applied. This may be a microtiter plate reader, an optical measurement apparatus or any similar apparatus.

The general structure of the apparatus 200 comprises a display 240, an optical component (e.g. filter or mirror) module 250 with component storages and a transfer mechanism, a communication interface 270, a movement sensor 280, a processor 210, and a memory 220 coupled to the processor 210. The apparatus 200 further comprises software 230 stored in the memory 220 and operable to be loaded into and executed in the processor 210. In some embodiments, the software 230 comprises one or more software modules and can be in the form of a computer program product. The apparatus 200 may further comprise a radiation (e.g. light) source 290, at least one detector 295 and optics 299. The apparatus 200 may still further comprise a user interface controller 260 coupled to the processor 210.

The processor 210 may be, e.g., a central processing unit (CPU), a microprocessor, a digital signal processor (DSP), a graphics processing unit, or the like. FIG. 2 shows one processor 210, but in some embodiments the apparatus 200 comprises a plurality of processors.

The memory 220 may be for example a non-volatile or a volatile memory, such as a read-only memory (ROM), a programmable read-only memory (PROM), erasable programmable read-only memory (EPROM), a random-access memory (RAM), a flash memory, a data disk, an optical storage, a magnetic storage, a smart card, or the like. In some embodiments, the apparatus 200 comprises a plurality of memories. The memory 220 may be constructed as a part of the apparatus 200 or it may be inserted into a slot, port, or the like of the apparatus 200 by a user. The memory 220 may serve the sole purpose of storing data, or it may be constructed as a part of an apparatus serving other purposes, such as processing data.

The optical component module 250 may comprise at least one storage for optical components usable in the apparatus 200 and a component transfer mechanism that all can be driven and controlled based on the program code 230 and the processor 210. The component module 250 may also comprise dedicated measurement position outside the component storage.

The movement sensor 280 may be included in the apparatus 200 for sensing a used position of the component storage.

The communication interface module 270 implements at least part of the data transmission from the apparatus 200 to an external apparatus or system for various embodiments of the invention. The communication interface module 270 may be, e.g., a fixed interface module, such as a LAN, or a radio interface module, such as a WLAN, Bluetooth, GSM/GPRS, CDMA, WCDMA, or LTE (Long Term Evolution) radio module. The communication interface module 270 may be integrated into the apparatus 200 or into an adapter, card or the like that may be inserted into a suitable slot or port of the apparatus 200. The communication interface module 270 may support one radio interface technology or a plurality of technologies. FIG. 2 shows one communication interface module 270, but in some embodiments the apparatus 200 comprises a plurality of communication interface modules 270.

The display 240 may be for example a liquid crystal display (LCD) or a light-emitting diode (LED) based display. A touch-sensitive surface may be integrated to the display 240 as a touch display or a touch screen. The touch-sensitive surface may also be included as a separate element, for example as a touchpad.

The user interface controller 260 comprises circuitry for receiving input from a user of the apparatus 200, e.g., via a keyboard, graphical user interface shown on the display 240 of the apparatus 200, speech recognition circuitry, or an accessory device, such as a headset, and for providing output to the user via, e.g., a graphical user interface or a loudspeaker.

The radiation source 290 may be a polychromatic light source, such as a halogen lamp, for example. The optics 299 may comprise at least one lens that may be positioned between the light source 290 and a detector 295. The detector 295 may be a photoelectric detector or a photometer, for example, converting light into an electrical signal for processing.

A skilled person appreciates that in addition to the elements shown in FIG. 2, in some embodiments the apparatus 200 comprises other elements, such as microphones, extra displays, as well as additional circuitry such as input/output (I/O) circuitry, memory chips, application-specific integrated circuits (ASIC), processing circuitry for specific purposes such as source coding/decoding circuitry, channel coding/decoding circuitry, ciphering/deciphering circuitry, and the like. Additionally, the apparatus 200 comprises a disposable or rechargeable battery (not shown) for powering the apparatus 200 if external power supply is not available. Another option is to use a capacitor instead of the battery for powering the apparatus 200 if external power supply is not available.

Figure 3:
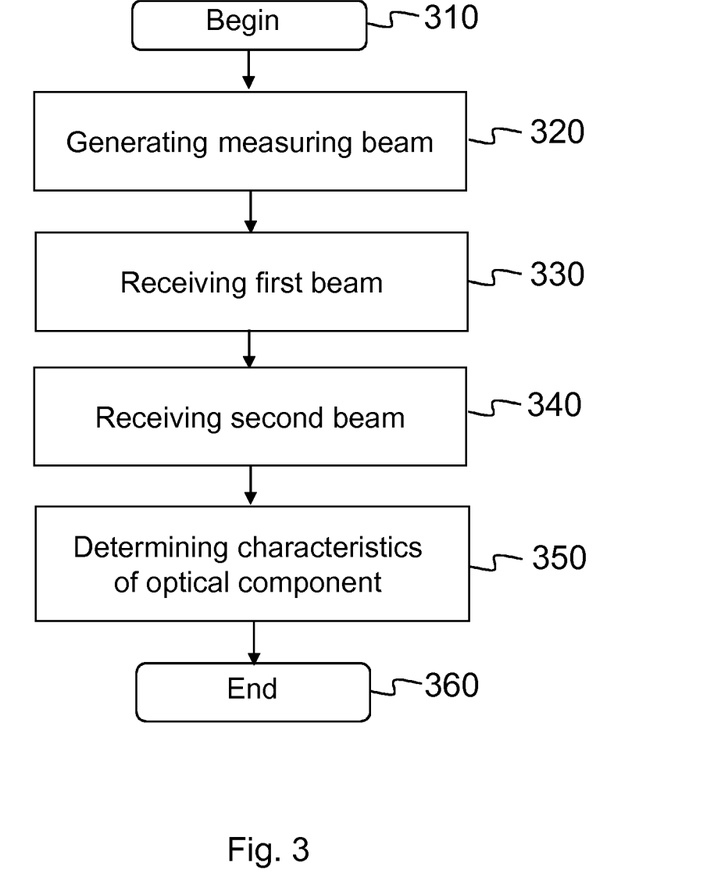
FIG. 3 shows a flow chart of a method in accordance with an example embodiment of the invention.

FIG. 3 shows an example flow chart of a method in accordance with an example embodiment of the invention. The method begins at block 310. In block 320, a measuring beam is generated in a measuring channel using a radiation source. A first beam is received, using a first detector, in the measuring channel in step 330, wherein the measured optical component is in a first position outside the measuring channel. In step 340, a second beam is received, using the first detector, in the measuring channel, wherein the measured optical component is in a second position in the measuring channel. In step 350, the characteristics of the optical component are determined based on the first beam and the second beam. The method ends at block 360. The example method presented in the foregoing is an example only. In other embodiments, different functions in the method may occur in a mutually different order.

Various embodiments have been presented. It should be appreciated that in this document, words comprise, include and contain are each used as open-ended expressions with no intended exclusivity.

The foregoing description has provided by way of non-limiting examples of particular implementations and embodiments of the invention a full and informative description of the best mode presently contemplated by the inventors for carrying out the invention. It is however clear to a person skilled in the art that the invention is not restricted to details of the embodiments presented above, but that it can be implemented in other embodiments using equivalent means or in different combinations of embodiments without deviating from the characteristics of the invention.

Furthermore, some of the features of the above-disclosed embodiments of this invention may be used to advantage without the corresponding use of other features. As such, the foregoing description shall be considered as merely illustrative of the principles of the present invention, and not in limitation thereof. Hence, the scope of the invention is only restricted by the appended patent claims.

The invention claimed is:

1. A microtiter late reader apparatus for measuring an optical component of the apparatus, the apparatus comprising:
    a light source configured to form a measuring beam in a measuring channel, wherein the measured optical component configured to be in a first position outside the measuring channel and in a second position in the measuring channel;
    a first detector, located in the measuring channel, configured to receive beams in the measuring channel, wherein the measuring channel being integrated to a photometer channel or a fluorescence channel of the apparatus, wherein the photometer channel or the fluorescence channel being used when measuring a sample using the apparatus;
    at least one processor; and
    at least one memory including computer program code, the at least one memory and the computer program code being configured to, with the at least one processor, cause the apparatus at least to:
        measure a first beam, using the first detector, in the measuring channel, wherein the measured optical component is in the first position;
        measure a second beam, using the first detector, in the measuring channel, wherein the measured optical component is in the second position between the light source and the first detector; and
        determine optical characteristics of the optical component based on the first beam and the second beam.

2. The apparatus of claim 1, the at least one memory and the computer program code being further configured to, with the at least one processor, cause the apparatus to:
    store the characteristics of the optical component to the memory; and
    provide the optical component to be used by a user of the apparatus.

3. The apparatus of claim 1, wherein the optical component being a filter, band-passing the second beam to the first detector; and
    the at least one memory and the computer program code being further configured to, with the at least one processor, cause the apparatus to:
    determine the characteristics of the filter based on the first beam and the second beam, wherein the characteristics comprise band-pass wavelength information.

4. The apparatus of claim 1, wherein the optical component being a dichroic mirror, reflecting the second beam to the first detector; and
    the at least one memory and the computer program code being further configured to, with the at least one processor, cause the apparatus to:
    determine the characteristics of the dichroic mirror based on the first beam and the second beam, wherein the characteristics comprise reflection wavelength information.

5. The apparatus of claim 1, wherein the optical component being a dichroic mirror, transmitting the second beam to the first detector; and
    the at least one memory and the computer program code being further configured to, with the at least one processor, cause the apparatus to:
    determine the characteristics of the dichroic mirror based on the first beam and the second beam, wherein the characteristics comprise transmittance wavelength information.

6. The apparatus of claim 1, wherein the first detector comprising at least one of the following:
    a photometer detector;
    a fluorescence detector;
    a spectrograph;
    a photo multiplier tube; and
    a photodiode.

7. The apparatus of claim 1, wherein the measuring channel comprising at least one of the following:
   a fluorescence channel of a microtiter plate reader;
   a photometer channel of a microtiter plate reader;
   an emission channel of a microtiter plate reader; and
   an excitation channel of a microtiter plate reader.

8. The apparatus of claim 1, wherein the first position comprising a storage position for the optical component in the apparatus.

9. The apparatus of claim 1, further comprising a second detector configured to receive beams in the measuring channel;
   the at least one memory and the computer program code being further configured to with the at least one processor, cause the apparatus to:
   select at least one of the first detector and the second detector to receive beams in the measuring channel, wherein the second detector comprising at least one of the following:
      a photomultiplier tube; and
      a photo diode.

10. The apparatus of claim 1, wherein the light source is configured, together with an excitation filter of certain optical characteristics, to generate a desired excitation light.

11. The apparatus of claim 7, further comprising optics comprising at least one lens positioned between the light source and at least one detector to focus and re-size the light beam to a desired size and separate channels.

12. A method for measuring characteristics of an optical component of a microtiter plate reader apparatus, the method comprising:
   generating a measuring beam in a measuring channel using a light source; wherein a first detector being configured to receive beams in the measuring channel, the measuring channel being integrated to a photometer channel or a fluorescence channel of the apparatus, wherein the photometer channel or the fluorescence channel being used when measuring a sample using the apparatus and the method further comprising:
   measuring a first beam, using the first detector, in the measuring channel, wherein the measured optical component is in a first position outside the measuring channel;
   measuring a second beam, using the first detector, in the measuring channel, wherein the measured optical component is in a second position inside the measuring channel between the light source and the first detector; and
   determining the optical characteristics of the optical component based on the first beam and the second beam.

13. A computer program embodied on a computer readable non-transitory medium comprising computer executable program code which, when executed by at least one processor of a microtiter plate reader apparatus, causes the apparatus to perform the method of claim 12.

14. The apparatus of claim 1, wherein the at least one memory and the computer program code being further configured to, with the at least one processor, cause the apparatus to:
   identify the optical component based on the determined optical characteristics.

* * * * *